(12) United States Patent
Morita et al.

(10) Patent No.: US 11,976,020 B2
(45) Date of Patent: May 7, 2024

(54) METHOD FOR PRODUCING (METH)ACRYLIC ACID AMIDE COMPOUND, COMPOSITION, AND ACTIVE ENERGY RAY-CURABLE COMPOSITION

(71) Applicants: Mitsunobu Morita, Shizuoka (JP); Masahide Kobayashi, Kanagawa (JP); Takenori Suenaga, Tochigi (JP); Soh Noguchi, Kanagawa (JP); Takashi Okada, Kanagawa (JP)

(72) Inventors: Mitsunobu Morita, Shizuoka (JP); Masahide Kobayashi, Kanagawa (JP); Takenori Suenaga, Tochigi (JP); Soh Noguchi, Kanagawa (JP); Takashi Okada, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 400 days.

(21) Appl. No.: 17/302,798

(22) Filed: May 12, 2021

(65) Prior Publication Data

US 2021/0355075 A1   Nov. 18, 2021

(30) Foreign Application Priority Data

May 14, 2020   (JP) ................................ 2020-085118
Sep. 7, 2020   (JP) ................................ 2020-149953

(51) Int. Cl.
| C07C 231/02 | (2006.01) |
| C08K 5/20 | (2006.01) |
| C08L 33/26 | (2006.01) |

(52) U.S. Cl.
CPC .............. *C07C 231/02* (2013.01); *C08K 5/20* (2013.01); *C08L 33/26* (2013.01)

(58) Field of Classification Search
CPC ....... C07C 231/02; C07C 233/49; C08K 5/20; C08L 33/26; C09D 4/00; C07D 207/16; C08F 220/54
USPC ...................................... 528/332, 271; 520/1
See application file for complete search history.

(56) References Cited

U.S. PATENT DOCUMENTS

| 4,206,143 A | 6/1980 | Wenzel et al. |
| 5,962,578 A | 10/1999 | Beihoffer et al. |
| 10,174,215 B2 | 1/2019 | Morita et al. |
| 2018/0127607 A1 * | 5/2018 | Morita ................. C07C 233/00 |
| 2020/0010662 A1 * | 1/2020 | Hiraoka ............... C08K 5/0025 |
| 2020/0031969 A1 | 1/2020 | Kobayashi et al. |
| 2020/0032068 A1 | 1/2020 | Yamaguchi et al. |
| 2020/0032089 A1 | 1/2020 | Kobayashi et al. |
| 2020/0038309 A1 | 2/2020 | Suenaga et al. |
| 2020/0038310 A1 | 2/2020 | Suenaga et al. |
| 2020/0299425 A1 | 9/2020 | Kobayashi et al. |
| 2020/0308425 A1 | 10/2020 | Noguchi et al. |
| 2021/0061929 A1 | 3/2021 | Kobayashi et al. |
| 2021/0122938 A1 | 4/2021 | Kobayashi et al. |

FOREIGN PATENT DOCUMENTS

| EP | 3321333 | 5/2018 |
| JP | H07-330701 | 12/1995 |
| JP | 3160605 B2 | 2/2001 |
| JP | 2016-125008 | 7/2016 |
| JP | 2018-104365 | 7/2018 |
| JP | 2018-168209 | 11/2018 |
| JP | 2019-019309 | 2/2019 |
| JP | 2019-156734 | 9/2019 |
| JP | 2019156734 | * 9/2019 |
| WO | 99/25394 | 5/1999 |
| WO | 2020/026675 | 2/2020 |

OTHER PUBLICATIONS

Kobayashi et al, JP 2019156734 Machine Translation, Sep. 19, 2019 (Year: 2019).*
Extended European Search Report dated Sep. 27, 2021 in European Application No. 21173744.0, 6 pages.
Wojcik, J. et al., Conformational Analysis of Some Acrylamide Homologues, Bulletin de l'Academie Polonaise des Sciences. Serie des Sciences Chimiques, 1980, vol. 28, pp. 613-619.
New Experimental Chemistry Course 14 (ed. the Chemical Society of Japan), pp. 1138-1139.
Japanese First Office Action dated Oct. 12, 2020 for the corresponding Japanese Application No. 2020-149953.
U.S. Appl. No. 17/126,409, filed Dec. 18, 2020.

* cited by examiner

*Primary Examiner* — Jessica Whiteley
(74) *Attorney, Agent, or Firm* — Grüneberg and Myers PLLC

(57) ABSTRACT

A method for producing a (meth)acrylic acid amide compound, the method including: adding at least one selected from the group consisting of an amino group-containing compound and a neutralization salt of the amino group-containing compound to a mixture including (meth)acrylic acid halide and an organic solvent immiscible with water to allow the (meth)acrylic acid halide and at least one selected from the group consisting of the amino group-containing compound and the neutralization salt of the amino group-containing compound to react with each other, to produce the (meth)acrylic acid amide compound.

17 Claims, 11 Drawing Sheets

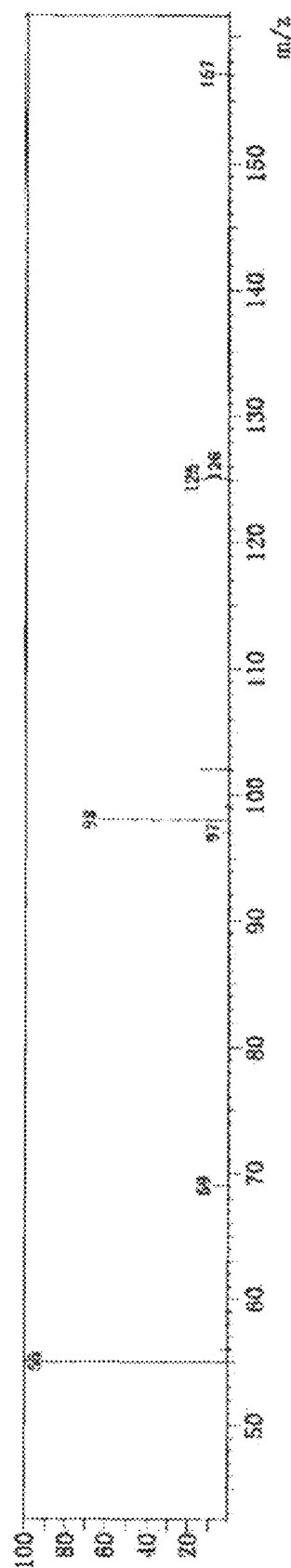

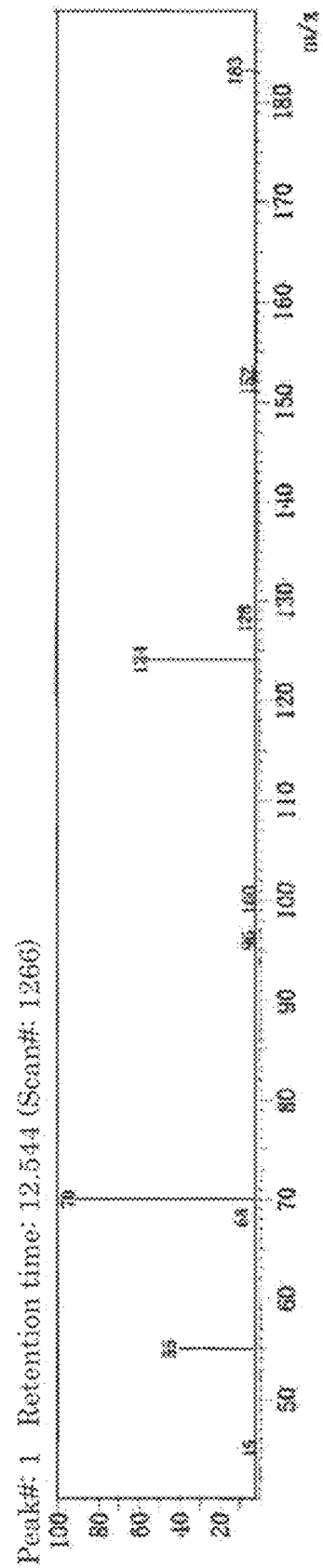

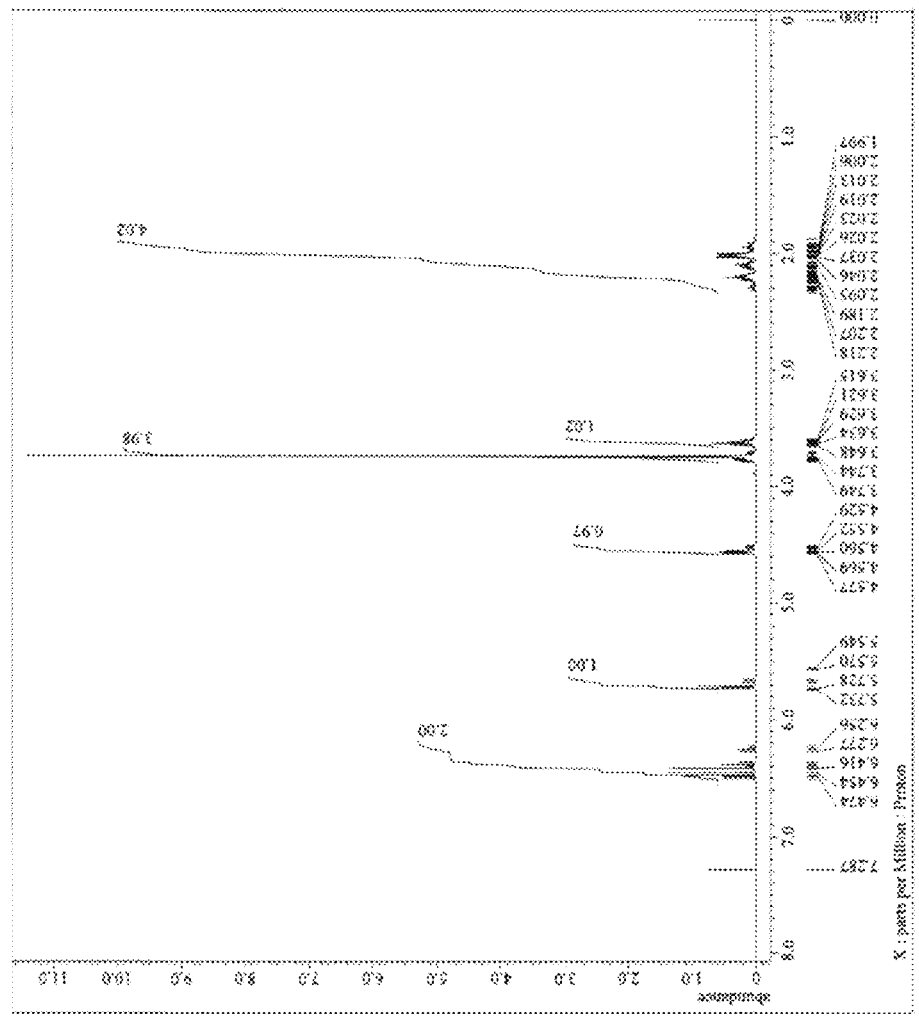

US 11,976,020 B2

METHOD FOR PRODUCING (METH)ACRYLIC ACID AMIDE COMPOUND, COMPOSITION, AND ACTIVE ENERGY RAY-CURABLE COMPOSITION

CROSS-REFERENCE TO RELATED APPLICATIONS

The present application claims priority under 35 U.S.C. § 119 to Japanese Patent Application No. 2020-085118 filed May 14, 2020, and Japanese Patent Application No. 2020-149953 filed Sep. 7, 2020. The contents of which are incorporated herein by reference in their entirety.

BACKGROUND OF THE INVENTION

Field of the Invention

The present disclosure relates to a method for producing (meth)acrylic acid amide compound, a composition, and an active energy ray-curable composition.

Description of the Related Art

A method for producing an amide compound (acid amide compound) is generally roughly classified into two methods, which are a method using redox reactions, and a method for producing from carboxylic acid or a carboxylic acid-derived compound. As the latter method, there are various production methods using a wide variety of raw materials. For examples, there are a method where an acid amide compound is produced from carboxylic acid and an amino compound (amine) using various condensing agents, and a method where carboxylic acid halide is used instead of carboxylic acid.

Among the above-mentioned methods, a method using carboxylic acid halide (e.g., carboxylic acid chloride) does not require a condensing agent, and is a method suitably for production of a large scale as a reaction progresses quantitatively at a low temperature (see WOJCIK, J et al., Conformational Analysis of Some Acrylamide Homologues, Bulletin de l'Academie Polonaise des Sciences. Serie des Sciences Chimiques, 1980, Vol. 28, pp. 613-619). Moreover, a method so-called Schotten-Baumann reaction, where carboxylic acid halide is added to a mixture of an amino compound (amine) and an alkali aqueous solution by dripping, is also known as a method excels in yield and purity (see New Experimental Chemistry Course 14 (ed. the Chemical Society of Japan), pp. 1138-1139). As a production example of a (meth)acrylamide compound using carboxylic acid halide, disclosed is a production method where acrylic acid chloride is added to a THF solution of 3-aminopropionitrile and triethyl amine by dripping (see Japanese Unexamined Patent Application Publication No. 2018-168209).

The above document by WOJCIK, J et al. describes about analysis of an acryl amide analog, and discloses, as a general scheme of amide synthesis, a method where an amine ether solution is added to an acid chloride ether solution.

SUMMARY OF THE INVENTION

According to an aspect of the present disclosure, a method for producing a (meth)acrylic acid amide compound includes adding at least one selected from the group consisting of an amino group-containing compound and a neutralization salt of the amino group-containing compound to a mixture including (meth)acrylic acid halide and an organic solvent immiscible with water to allow the (meth)acrylic acid halide and at least one selected from the group consisting of the amino group-containing compound and the neutralization salt of the amino group-containing compound to react with each other.

BRIEF DESCRIPTION OF THE DRAWINGS

FIG. 1C is a diagram representing the retention time, peak area, and area % of each peak of FIG. 1A;
FIG. 2A is an MS chart for peaks with the retention time of 10.8 minutes detected in the GC-MS chromatogram of the compound obtained in Example 1-5;
FIG. 4C is a diagram representing the retention time, peak area, and area % of each peak of FIG. 4A;
FIG. 5A is an MS chart for peaks with the retention time of 12.5 minutes detected in the GC-MS chromatogram of the compound obtained in Example 1-8;
FIG. 6 is a $^1$H-NMR chart of the compound obtained in Example 1-8.

DESCRIPTION OF THE EMBODIMENTS

Figure 1A:
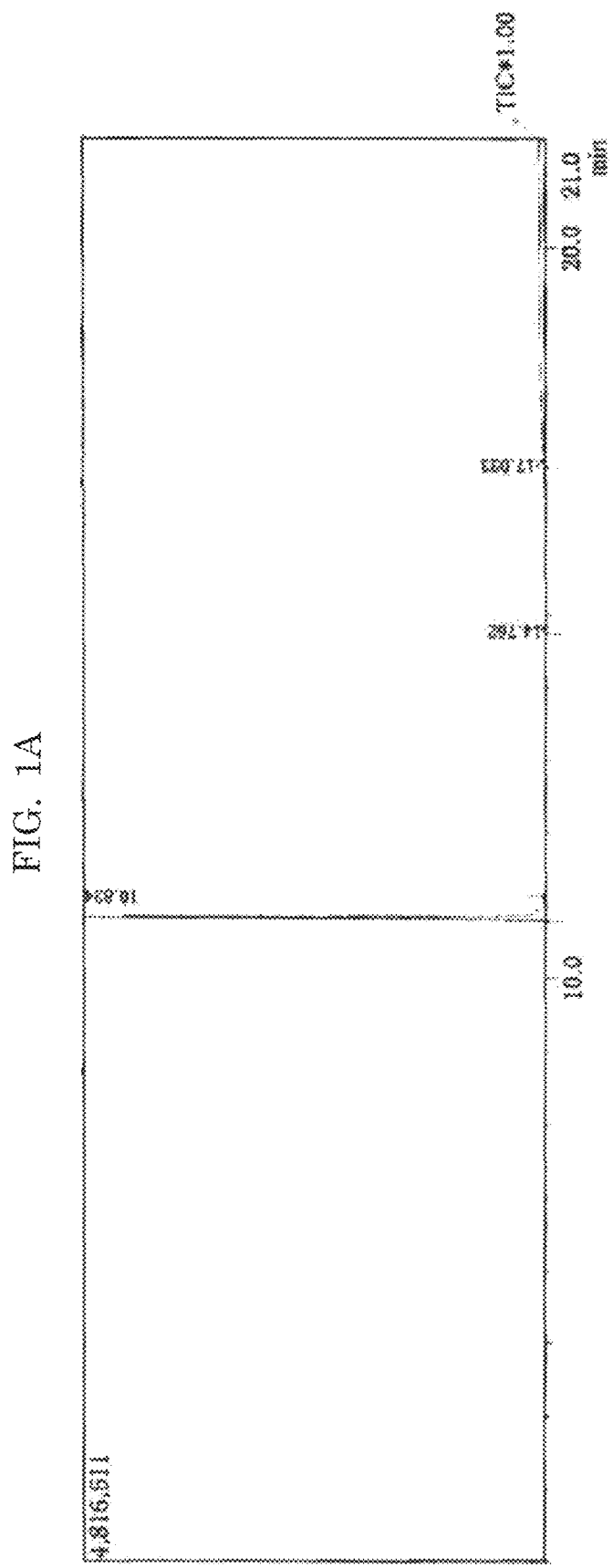
FIG. 1A is a GC-MS chromatogram of the compound obtained in Example 1-5.

The present disclosure is directed to the (1) method for producing a (meth)acrylic acid amide compound below, but embodiments thereof include the following (2) to (12) below, which will be also described together with (1).

(1) A method for producing a (meth)acrylic acid amide compound, the method including
adding at least one selected from the group consisting of an amino group-containing compound and a neutralization salt of the amino group-containing compound to a mixture including (meth)acrylic acid halide and an organic solvent immiscible with water to allow the (meth)acrylic acid halide and at least one selected from the group consisting of the amino group-containing compound and the neutralization salt of the amino group-containing compound to react with each other, to produce the (meth)acrylic acid amide compound.

(2) The method according to (1), wherein at least one selected from the group consisting of the amino group-containing compound and the neutralization salt of the amino group-containing compound is an aqueous solution of at least one selected from the group consisting of the amino group-containing compound and the neutralization salt of the amino group-containing compound.
(3) The method according to (1) or (2), further including adding an alkaline aqueous solution after adding at least one selected from the group consisting of the amino group-containing compound and the neutralization salt of the amino group-containing compound to the mixture.
(4) The method according to any one of (1) to (3), wherein solubility of the organic solvent in water is 30 g/100 mL or less.
(5) The method according to any one of (1) to (4), wherein the solubility of the organic solvent in water is 2 g/100 mL or greater but 30 g/100 mL or less.
(6) The method according to any one of (1) to (5), wherein the organic solvent is at least one selected from the group consisting of ethyl acetate, toluene, cyclopentyl methyl ether, butyl acetate, and methyl ethyl ketone.
(7) The method according to any one of (1) to (6), wherein the organic solvent is ethyl acetate.
(8) The method according to any one of (1) to (7), wherein at least one selected from the group consisting of the amino group-containing compound and the neutralization salt of the amino group-containing compound is a compound including an amino group and a carboxylic acid ester structure.
(9) The method according to (8), wherein the compound including an amino group and a carboxylic acid ester structure is an amino acid derivative having sarcosine as a mother nucleus.
(10) The method according to (8), wherein the compound including an amino group and a carboxylic acid ester structure is an amino acid derivative having proline as a mother nucleus.
(11) A composition including:
a (meth)acrylic acid amide compound; and
an adduct of a (meth)acrylic acid amide compound and an amino group-containing compound,
wherein an amount of the (meth)acrylic acid amide compound is 95% by mass or greater, and an amount of the adduct of the (meth)acrylic acid amide compound and the amino group-containing compound is less than 5% by mass.
(12) An active energy ray-curable composition including:
the composition according to (11).

(Method for Producing (Meth)Acrylic Acid Amide Compound)

In the method for producing acid amide using acid halide, such as carboxylic acid chloride, an alkali compound that neutralizes hydrogen chloride generated by a reaction is provided to accelerate the reaction, and therefore a target material is obtained at high yield (see the following reaction scheme (1)).

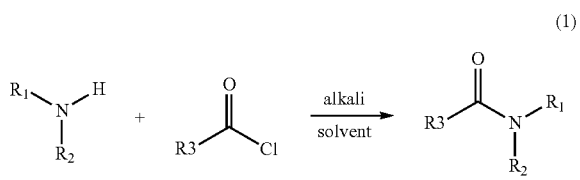

(1)

When the reaction above is applied for acrylamide, an acrylic acid amide compound can be synthesized as presented in the following reaction scheme (2). In the reaction below, however, an addition reaction between the generated acrylic acid amide compound and an amino compound (amine), which is a raw material, is progressed as presented in the reaction scheme (3) below to lower yield and purity of the acrylic acid amide.

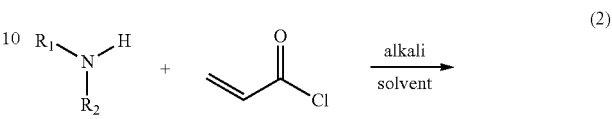

(2)

(3)

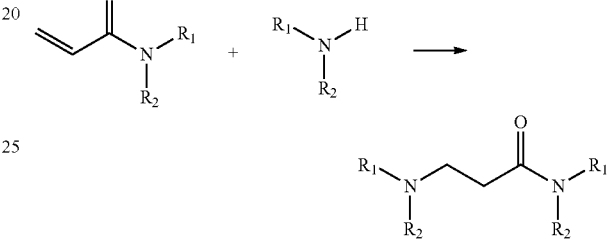

An amidation reaction between acid halide, such as carboxylic acid chloride, and an amino compound causes vigorous foaming and generates heat, and therefore the reaction is performed by dripping carboxylic acid chloride little by little with cooling the reaction system in order to prevent rapid increase in the reaction temperature and vigorous foaming. In this case, the generated acryl amide compound and the amino compound (amine), which is a raw material, coexist in the reaction system, and therefore an addition reaction according to the reaction scheme (3) tends to be progressed. More slowly the carboxylic acid chloride is dripped in order to perform the reaction mildly, more likely reduction in yield and purity is caused by the progress of the addition reaction.

According to the conventional method where a (meth) acrylic acid amide compound is produced from an amino compound (amine) and (meth)acrylic acid chloride, there is a problem that a side reaction (Michael addition) where the amino compound (amine), which is a raw material, is added to an unsaturated double bond of the generated (meth)acrylic acid amide, tends to progress, lowing yield and purity (see Japanese Unexamined Patent Application Publication No. 2018-168209).

When an organic solvent, such as ether is used alone as a solvent, moreover, there is a problem that, as purity of a crude product is low, distillation or recrystallization needs to be performed on the crude product in order to achieve high purity (see WOJCIK, J et al., Conformational Analysis of Some Acrylamide Homologues, Bulletin de l'Academie Polonaise des Sciences. Serie des Sciences Chimiques, 1980, Vol. 28, pp. 613-619).

Therefore, it is possible to suppress the progress of the addition reaction through dripping of the acrylic acid chloride within a short period of time. The yield and purity can be both actually improved by dripping the acrylic acid chloride at once within a short period of time. However, hydrogen chloride gas is vigorously bubbled inside the reaction vessel and the reaction temperature is also rapidly increased. Therefore, the reaction cannot be controlled, and an accident is more likely to occur. Therefore, such a method is not suitable as a production method of a large reaction scale.

The present disclosure has an object to provide a method for producing a (meth)acrylic acid amide compound, where the method can produce a (meth)acrylic acid amide compound of high purity with high yield, while suppressing an addition reaction (Michael addition reaction) of an amino compound to generated (meth)acrylic acid amide in the course of a method for synthesizing a (meth)acrylic acid amide compound from (meth)acrylic acid halide and at least one selected from the group consisting of an amino group-containing compound and a neutralization salt of the amino group-containing compound.

Under such circumstances, according to the synthesis method of the present disclosure, a reaction vessel is charged with a mixture including acid halide, such as (meth)acrylic acid chloride, and a solvent immiscible with water in advance, followed by adding at least one selected from the group consisting of an amino group-containing compound and a neutralization salt of the amino group-containing compound. Specifically, in the synthesis method of the present disclosure, acid halide is housed in the reaction vessel, and at least one selected from the group consisting of an amino group-containing compound and a neutralization salt of the amino group-containing compound is added to the reaction vessel. Compared with a synthesis method known in the art, where at least one selected from the group consisting of an amino group-containing compound and a neutralization salt of the amino group-containing compound is stored in a reaction vessel, followed by adding acid halide to the reaction vessel, a relationship between the contents of the reaction vessel and the material added to the reaction vessel is reversed. Moreover, the method of the present disclosure is different from the method known in the art in that the reaction system is a non-homogeneous mixed solvent system including a solvent immiscible with water and water.

In the present disclosure, moreover, a neutralization salt, such as hydrochloride of an amino group-containing compound can be used as at least one selected from the group consisting of the amino group-containing compound and the neutralization salt of the amino group-containing compound. Moreover, the amino group-containing compound may be added as an amino group-containing compound aqueous solution, where the amino group-containing compound is neutralized with alkali, into a reaction vessel by dripping.

Moreover, an amidation reaction may be carried out by adding an aqueous solution of a neutralization salt of the amino group-containing compound to the mixture including the (meth)acrylic acid chloride and the solvent immiscible with water, followed by adding an alkali aqueous solution, or adding a solid neutralization salt of the amino group-containing compound to the mixture including the (meth)acrylic acid chloride and the solvent immiscible with water, followed by adding an alkali aqueous solution. In either case, the amino group-containing compound added or generated in the reaction system is immediately consumed by the reaction with the (meth)acrylic acid chloride, a large amount of which is present, to generate a (meth)acrylic acid amide compound. Therefore, the generated (meth)acrylic acid amide compound and the amino group-containing compound are unlikely to coexist, and a state where an addition reaction, which is a side reaction, is unlikely to be progressed may be created. Moreover, the reaction system at the time when the amidation reaction is progressed is a non-homogeneous mixed solvent system including the solvent immiscible with water and water, and the amidation reaction is progressed at an interface between the solvent and the water. Therefore, the reaction is progressed very mildly compared with the conventional homogeneous solvent system including carboxylic acid halide and an amino compound. Accordingly, the synthesis can be performed safely with a large scale, and therefore the method of the present disclosure is a suitable method for industrialization.

In the present disclosure, the term "(meth)acrylic acid amide compound" means an acrylic acid amide compound and a methacrylic acid amide compound.

The present disclosure can provide a method for producing a (meth)acrylic acid amide compound, where the method can produce a (meth)acrylic acid amide compound of high purity with high yield, while suppressing an addition reaction (Michael addition reaction) of an amino compound to generated (meth)acrylic acid amide in the course of a method for synthesizing a (meth)acrylic acid amide compound from (meth)acrylic acid halide and at least one selected from the group consisting of an amino group-containing compound and a neutralization salt of the amino group-containing compound.

Various materials used for the synthesis method of the present disclosure will be described hereinafter.

In the present disclosure, the term "(meth)acrylic acid halide" means acrylic acid halide and methacrylic acid halide.

As the (meth)acrylic acid halide, typically, acrylic acid chloride or methacrylic acid chloride, which is chloride of (meth)acrylic acid, is used, but other halides, such as bromide, may be used. Among the above-listed examples, acrylic acid chloride and methacrylic acid chloride are preferable in view of readily availability of raw materials thereof.

The organic solvent immiscible with water is used as a solvent for diluting the (meth)acrylic halide. In the present disclosure, the term "solvent immiscible with water" means a solvent that cannot form a homogeneous solution when mixed with water at a predetermined ratio, and does not mean that such a solvent is insoluble in water. The solubility of the solvent immiscible with water in water cannot be clearly defined, but the solvent immiscible with water is generally a solvent having the solubility of about 30 g/100 mL or less, preferably 2 g/100 mL or greater but 30 g/100 mL or less.

As the solvent immiscible with water, an organic solvent that does not react with acid halide can be appropriately used. Examples of such an organic solvent include: aliphatic hydrocarbon-based solvents, such as pentane, hexane, heptane, and octane; aromatic hydrocarbon-based solvents, such as benzene, toluene, and xylene; ester-based solvents, such as methyl acetate, ethyl acetate, butyl acetate, isobutyl acetate, n-butyl acetate, isopropyl acetate, n-propyl acetate, isopentyl acetate, and n-pentyl acetate; ether-based solvents, such as dimethyl ether, diethyl ether, cyclopentyl methyl ether, ethylene glycol monoethyl ether acetate (cellosolve acetate), and ethylene glycol-mono-butyl ether (butyl cellosolve); and ketone-based solvents, such as methyl ethyl ketone (MEK), methyl isobutyl ketone, methyl n-butyl ketone, cyclohexanone, and methyl cyclohexanone. Among the above-listed examples, the ester-based solvents, ketone-based solvents, and ether-based solvents are preferable because of excellent solubility to raw materials and generated products therefrom. Among them, ethyl acetate and methyl ethyl ketone (MEK) are preferably used. The above-listed solvents may be used alone or as a mixture.

Examples of at least one selected from the group consisting of the amino group-containing compound and the neutralization salt of the amino group-containing compound include a compound having an amino group and a carboxylic acid ester structure. Examples of the compound having an amino group and a carboxylic acid ester structure include: an amino acid derivative having sarcosine as a mother nucleus, such as sarcosine methyl ester-hydrochloride, and sarcosine ethyl ester-hydrochloride; and an amino acid derivative having proline as a mother nucleus, such as proline methyl ester-hydrochloride, and proline ethyl ester-hydrochloride.

The alkali aqueous solution is used for the purpose of neutralizing acid (acid, such as hydrogen chloride) generated as a result of a reaction between acid halide and an amino group-containing compound, or neutralizing an acid forming a neutralization salt of the amino group-containing compound, which is a raw material, to liberate an amino group. As the alkali in such an alkali aqueous solution, various alkali, such as organic alkali and inorganic alkali, can be used. For example, inorganic alkali (e.g., sodium hydroxide, potassium hydroxide, potassium carbonate, and sodium carbonate), and a tertiary amine compound (e.g., triethyl amine, trimethyl amine, and pyridine) can be used. Among the above-listed examples, water-soluble alkali is preferable. Among them, inorganic weak alkali, such as sodium carbonate, is preferable as a neutralization reaction is carried out mildly.

In the case where an aqueous solution of an amino group-containing compound is added, or a neutralization salt of an amino group-containing compound in the form of an aqueous solution or solids is added to the mixture including the (meth)acrylic acid halide and the organic solvent immiscible with water, an amidation reaction is progressed by adding the alkali. For the addition, duration for dripping at least one selected from the group consisting of the amino group-containing compound and the neutralization salt thereof is not particularly limited as the duration depends on a reaction scale. The amino group-containing compound or the neutralization salt thereof is appropriately dripped within the time period by which the (meth)acrylic acid halide is not deactivated, and is preferably dripped within a short period of time.

At the time of the reaction, the temperature increases due to generation of heat. The temperature range during the reaction needs to be equal to or lower than a boiling point of the solvent for use. The temperature is adjusted by cooling generally at 50° C. or lower, preferably 30° C. or lower.

(Composition of (Meth)Acrylic Acid Amide Compound and Active Energy Ray-Curable Composition)

The method for producing a (meth)acrylic acid amide compound according to the present disclosure, a side reaction is suppressed, and a (meth)acrylic acid amide compound of high purity can be produced with high yield. According to the method for producing a (meth)acrylic acid amide compound of the present disclosure, therefore, a composition including a (meth)acrylic acid amide compound in an amount of 95% by mass or greater, and an adduct of a (meth)acrylic acid amide compound and an amino group-containing compound in an amount of less than 5% by mass or less can be obtained.

The (meth)acrylic acid amide compound is a polymerizable monomer that is polymerized upon irradiation of active energy rays. Accordingly, an active energy ray-curable composition, which includes a composition including the (meth) acrylic acid amide compound of the present disclosure as a polymerizable component, has low viscosity, and excellent curability and adhesion, as the amount of the non-polymerizable adduct generated by a side reaction is small.

<Active Energy Rays>

Active energy rays used for curing the active energy ray-curable composition of the present disclosure are not particularly limited, and may be UV rays, electron beams, α-rays, δ-rays, γ-rays, and X-rays, as long as it can apply energy necessary for carrying out a polymerization reaction of the polymerizable component in the composition. In the case where a light source of particularly high energy is used, a polymerization reaction can be carried out without a polymerization initiator. In case of UV irradiation, moreover, use of no mercury is strongly desired in view of the protection of the environment. Use of a GaN-based semiconductor UV emission device instead of a mercury-based emitter is very effective industrially and environmentally. Moreover, UV light emitting diode (UV-LED) and UV light laser diode (UV-LD) are small and low cost, and have a long service life and high efficiency, and therefore preferable as a UV light source.

<Preparation of Active Energy Ray-Curable Composition>

The active energy ray-curable composition of the present disclosure can be produced using the above-mentioned various components, and production methods or conditions thereof are not particularly limited. For example, a polymerizable monomer, a pigment, a disperser, etc. are loaded in a disperser (e.g., a ball mill, a kitty mill, a disk mill, a pin mill, and a Dyno Mill) and are dispersed to prepare a pigment dispersion liquid, and the pigment dispersion liquid is further blended with a polymerizable monomer, an initiator, a polymerization inhibitor, a surfactant, etc. to prepare the active energy ray-curable composition.

<Viscosity>

The viscosity of the active energy ray-curable composition of the present disclosure may be appropriately adjusted depending on intended use or applicable unit, and is not particularly limited. In the case where the composition is applied for an ejection unit configured to eject the composition from a nozzle, for example, the viscosity at a temperature ranging from 20° C. through 65° C., ideally the viscosity at 25° C., is preferably from 3 mPa·s through 40 mPa·s, more preferably from 5 mPa·s through 15 mPa·s, and particularly preferably from 6 mPa·s through 12 mPa·s. Moreover, it is particularly preferred that the composition achieve the above-mentioned viscosity range without including the organic solvent. Note that, the viscosity can be measured by means of a cone and plate rotational viscometer, VISCOMETER TVE-22L, available from Toki Sangyo Co., Ltd. using a cone rotor (1°34'×R24) at the rotational speed of 50 rpm, and appropriately setting the temperature of the constant-temperature circulating water to the range of from 20° C. through 65° C. VISCOMATE VM-150III may be used for adjusting the temperature of the circulating water.

EXAMPLES

The present disclosure will be described below by way of Examples. The present disclosure should not be construed as being limited to these Examples.

In Examples below, effects of the present disclosure will be described by using sarcosine or proline, which is amino acid, as an amino group-containing compound, and using hydrochloride of a compound obtained by forming the carboxylic acid into methyl ether (sarcosine methyl ester-hydrochloride or L-proline methyl ester-hydrochloride) as a typical compound.

In Examples, the units "part(s)" and "%" denote "part(s) by mass" and "% by mass," respectively.

The structure of the obtained compound was confirmed by a $^1$H-NMR spectrum, and the amount of the obtained compound was confirmed by GC-MS.

[Synthesis of Sarcosine Methyl Ester-Hydrochloride]

Sarcosine (200 g, 2.245 mol, available from Tokyo Chemical Industry Co., Ltd.) was added to methyl alcohol (900 mL, available from Kanto Chemical Industry Co., Ltd.), and the resultant mixture was cooled to about −5° C. To the mixture, thionyl chloride (534 g, 4.49 mol, available from Kanto Chemical Industry Co., Ltd.) was slowly added by dripping. After the dripping, the mixture was stirred at room temperature. After confirming that the resultant reaction solution became clear, the solvent was removed by a rotary evaporator to thereby obtain white solids. The yielded amount was 312 g, and the yield on mass basis was about 100% by mass. Thus obtained sarcosine methyl ester-hydrochloride was used to study and synthesize the following acrylic acid amide compound (N-acryloyl sarcosine methyl ester).

Example 1-1

A 300 mL four-necked flask was charged with acrylic acid chloride (9.96 g, 110 mmol) and ethyl acetate (80 mL), and the mixture was cooled to a temperature ranging from −10° C. through −5° C. in an ice bath. A sarcosine methyl ester-hydrochloride aqueous solution [(13.96 g, 100 mmol)+(water: 40 mL)] and a potassium carbonate aqueous solution [(20.73 g, 150 mmol)+(water: 40 mL)] were mixed in a 300 mL beaker to prepare a sarcosine methyl aqueous solution. The resultant sarcosine methyl aqueous solution was added to the ethyl acetate solution of the acrylic acid chloride by dripping over 30 minutes. The temperature inside the reaction flask was −3° C. or lower. The resultant reaction liquid was extracted with ethyl acetate (80 mL) 3 times, and the extract was concentrated to thereby obtain a crude product of N-acryloyl sarcosine methyl ester.

Appearance: Colorless liquid
Yielded amount: 14.4 g,
Yield: 91.5% by mass
GC-MS Analysis
Amount of N-acryloyl sarcosine methyl ester: 97.1 area %
Adduct ratio: 0.2 area %
Other components: 2.7 area %

Example 1-2

A 3 L four-necked flask was charged with acrylic acid chloride (228 g, 2.52 mol, 1.1 eq.) and ethyl acetate (900 mL), and the mixture was cooled to a temperature ranging from −10° C. through −5° C. A sarcosine methyl ester-hydrochloride aqueous solution [(313.5 g, 2.245 mol)+(water: 500 mL)] and a potassium carbonate aqueous solution [(465.5 g, 3.37 mol)+(water: 800 mL)] were mixed in a 3 L beaker to prepare a sarcosine methyl aqueous solution. The resultant sarcosine methyl aqueous solution was added to the ethyl acetate solution of the acrylic acid chloride by dripping over 30 minutes. The temperature inside the reaction flask was 17° C. or lower. The resultant reaction liquid was extracted with ethyl acetate (900 mL) 3 times, and the extract was concentrated to thereby obtain a crude product of N-acryloyl sarcosine methyl ester.

Appearance: Pale yellow liquid
Yielded amount: 255.6 g,
Yield: 72.4% by mass
GC-MS Analysis
Amount of N-acryloyl sarcosine methyl ester: 86.5 area %
Adduct ratio: 9.5 area %
Other components: 4.0 area %

Example 1-3

A 200 mL four-necked flask was charged with acrylic acid chloride (9.96 g, 110 mmol) and ethyl acetate (80 mL), and a sarcosine methyl ester-hydrochloride aqueous solution [(13.96 g, 100 mmol)+(water: 40 mL)] was added to the resultant mixture with stirring, followed by cooling to a temperature ranging from −10° C. through −5° C. in an ice bath. Subsequently, a potassium carbonate aqueous solution [(20.73 g, 150 mmol)+(water: 40 mL)] was added to the resultant by dripping over 30 minutes. The temperature inside the reaction flask was 13° C. or lower. The resultant reaction liquid was extracted with ethyl acetate (80 mL) 3 times, and the extract was concentrated to thereby obtain a crude product of N-acryloyl sarcosine methyl ester.

Appearance: Colorless liquid
Yielded amount: 14.5 g
Yield: 92.2% by mass
GC-MS Analysis
Amount of N-acryloyl sarcosine methyl ester: 95.7 area %
Adduct ratio: 2.5 area %
Other components: 1.8 area %

Example 1-4

Synthesis was performed in the same manner as in Example 1-3, except that the duration for dripping the potassium carbonate aqueous solution was changed from 30 minutes to 10 minutes. The temperature inside the reaction flask was 15° C. or lower.

Appearance: Colorless liquid
Yielded amount: 14.7 g,
Yield: 93.8% by mass
GC-MS Analysis
Amount of N-acryloyl sarcosine methyl ester: 96.7 area %
Adduct ratio: 1.4 area %
Other components: 1.9 area %

Example 1-5

A 200 mL four-necked flask was charged with acrylic acid chloride (9.96 g, 110 mmol) and ethyl acetate (80 mL), and sarcosine methyl ester-hydrochloride solids (13.96 g, 100 mmol) were added to the resultant solution with stirring, followed by cooling to a temperature ranging from −10° C. through −5° C. in an ice bath. Subsequently, a potassium carbonate aqueous solution [(20.73 g, 150 mmol)+(water: 40 mL)] was added to the resultant by dripping over 10 minutes. The temperature inside the reaction flask was 20° C. or lower. The resultant reaction liquid was extracted with ethyl acetate (80 mL) 3 times, and the extract was concentrated to thereby obtain a crude product of N-acryloyl sarcosine methyl ester.

Appearance: Colorless liquid
Yielded amount: 15.7 g
Yield: 99.9% by mass
GC-MS Analysis Amount of N-acryloyl sarcosine methyl ester: 97.6 area %
Adduct ratio: 0.6 area %
Other components: 1.8 area %

Example 1-6

A 1 L four-necked flask was charged with acrylic acid chloride (49.8 g, 550 mmol) and ethyl acetate (400 mL), and sarcosine methyl ester-hydrochloride solids (69.8 g, 500 mmol) were added to the resultant mixture with stirring, followed by cooling to a temperature ranging from −10° C. through −5° C. in an ice bath. Subsequently, a potassium carbonate aqueous solution [(103.7 g, 750 mmol)+(water: 200 mL)] was added to the resultant by dripping over 10 minutes. The temperature inside the reaction flask was 11° C. or lower. The resultant reaction liquid was extracted with ethyl acetate (200 mL) 3 times, and the extract was concentrated to thereby obtain a crude product of N-acryloyl sarcosine methyl ester.
Appearance: Pale yellow liquid
Yielded amount: 77.7 g
Yield: 98.9% by mass
GC-MS Analysis
Amount of N-acryloyl sarcosine methyl ester: 99.8 area %
Adduct ratio: 0.0 area %
Other components: 0.2 area %

Example 1-7

A 3 L four-necked flask was charged with acrylic acid chloride (223.6 g, 2,470 mmol) and ethyl acetate (900 mL), and sarcosine methyl ester-hydrochloride solids (313 g, 2,242 mmol) were added to the resultant mixture with stirring, followed by cooling to a temperature ranging from −10° C. through −5° C. in an ice bath. Subsequently, a potassium carbonate aqueous solution [(465.5 g, 3.37 mol)+(water: 900 mL)] was added to the resultant by dripping over 10 minutes. The temperature inside the reaction flask was 12° C. or lower. The resultant reaction liquid was extracted with ethyl acetate (900 mL) 3 times, and the extract was concentrated to thereby obtain a crude product of N-acryloyl sarcosine methyl ester.
Appearance: Pale yellow liquid
Yielded amount: 342.4 g
Yield: 97.0% by mass
GC-MS Analysis
Amount of N-acryloyl sarcosine methyl ester: 99.7 area %
Adduct ratio: 0.0 area %
Other components: 0.3 area %

Example 1-8

A 3 L four-necked flask was charged with acrylic acid chloride (223.6 g, 2,470 mmol) and ethyl acetate (900 mL), and L-proline methyl ester-hydrochloride solids (378.1 g, 2,245 mmol, available from Combi-Brocks) were added to the resultant mixture with stirring, followed by cooling to a temperature ranging from −10° C. through −5° C. in an ice bath. Subsequently, a potassium carbonate aqueous solution [(465.5 g, 3.37 mol)+(water: 900 mL)] was added to the resultant by dripping over 15 minutes. The temperature inside the reaction flask was 26° C. or lower. The resultant reaction liquid was extracted with ethyl acetate (900 mL) twice, and the extract was concentrated to thereby obtain a crude product of N-acryloyl proline methyl ester.
Appearance: Pale yellow liquid
Yielded amount: 389.4 g
Yield: 94.7% by mass
GC-MS Analysis
Amount of N-acryloyl proline methyl ester: 99.5 area %
Adduct ratio: 0.0 area %
Other components: 0.5 area %

Example 1-9

A 1 L four-necked flask was charged with acrylic acid chloride (99.6 g, 1,100 mmol) and toluene (400 mL), and sarcosine methyl ester-hydrochloride solids (139.6 g, 1,000 mmol) were added to the resultant mixture with stirring, followed by cooling to a temperature ranging from −10° C. through −5° C. in an ice bath. Subsequently, a potassium carbonate aqueous solution [(207.3 g, 1.50 mol)+(water: 400 mL)] was added to the resultant by dripping over 10 minutes. The temperature inside the reaction flask was 15° C. or lower. The resultant reaction liquid was extracted with ethyl acetate (400 mL) 3 times, and the extract was concentrated to thereby obtain a crude product of N-acryloyl sarcosine methyl ester.
Appearance: Pale yellow liquid
Yielded amount: 145.7 g
Yield: 92.7% by mass
GC-MS Analysis
Amount of N-acryloyl sarcosine methyl ester: 98.1 area %
Adduct ratio: 1.9 area %
Other components: 0.0 area %

Example 1-10

A 1 L four-necked flask was charged with acrylic acid chloride (108.6 g, 1,200 mmol) and cyclopentyl methyl ether (400 mL), sarcosine methyl ester-hydrochloride solids (153.5 g, 1,100 mmol) were added to the resultant mixture with stirring, followed by cooling to a temperature ranging from −10° C. through −5° C. in an ice bath. Subsequently, a potassium carbonate aqueous solution [(228.1 g, 1.65 mol)+(water: 400 mL)] was added to the resultant by dripping over 10 minutes. The temperature inside the reaction flask was 15° C. or lower. The resultant reaction liquid was extracted with ethyl acetate (400 mL) 3 times, and the extract was concentrated to thereby obtain a crude product of N-acryloyl sarcosine methyl ester.
Appearance: Pale yellow liquid
Yielded amount: 160.3 g
Yield: 92.7% by mass
GC-MS Analysis
Amount of N-acryloyl sarcosine methyl ester: 99.2 area %
Adduct ratio: 0.8 area %
Other components: 0.0 area %

Example 1-11

A 1 L four-necked flask was charged with acrylic acid chloride (108.6 g, 1,200 mmol) and butyl acetate (400 mL), and sarcosine methyl ester-hydrochloride solids (153.5 g, 1,100 mmol) were added to the resultant mixture with stirring, followed by cooling to a temperature ranging from −10° C. through −5° C. in an ice bath. Subsequently, a potassium carbonate aqueous solution [(228.1 g, 1.65 mol)+(water: 400 mL)] was added to the resultant by dripping over 10 minutes. The temperature inside the reaction flask was 15° C. or lower. The resultant reaction liquid was extracted with ethyl acetate (400 mL) 3 times, and the extract was concentrated to thereby obtain a crude product of N-acryloyl sarcosine methyl ester.

Appearance: Pale yellow liquid
Yielded amount: 160.3 g
Yield: 89.5% by mass
GC-MS Analysis
Amount of N-acryloyl sarcosine methyl ester: 99.6 area %
Adduct ratio: 0.4 area %
Other components: 0.0 area %

Example 1-12

A 1 L four-necked flask was charged with acrylic acid chloride (99.6 g, 1,100 mmol) and methyl ethyl ketone (400 mL), L-proline methyl ester-hydrochloride solids (165.6 g, 1,000 mmol, available from Combi-Brocks) were added to the resultant mixture with stirring, followed by cooling to a temperature ranging from −10° C. through −5° C. in an ice bath. Subsequently, a potassium carbonate aqueous solution [(207.3 g, 1.50 mol)+(water: 400 mL)] was added to the resultant by dripping over 10 minutes. The temperature inside the reaction flask was 15° C. or lower. The resultant reaction liquid was extracted with ethyl acetate (400 mL) 3 times, and the extract was concentrated to thereby obtain a crude product of N-acryloyl proline methyl ester.
Appearance: Pale yellow liquid
Yielded amount: 180.1 g
Yield: 98.3% by mas
GC-MS Analysis
Amount of N-acryloyl proline methyl ester: 99.6 area %
Adduct ratio: 0.4 area %
Other components: 0.0 area %

Comparative Example 1-1

A 3 L four-necked flask was charged with sarcosine methyl ester-hydrochloride (312 g, 2,235 mmol) and water (900 mL), and the resultant was stirred to dissolve. To the resultant, a potassium carbonate aqueous solution [a solution where potassium carbonate (465 g, 3.37 mol, available from Kanto Chemical Industry Co., Ltd.) was dissolved in 900 mL of water] was added. The resultant reaction mixture was cooled to about 10° C. in an ice bath (ice cubes and sodium chloride), followed by slowly adding acrylic acid chloride (213.3 g, 2.36 mol, available from FUJIFILM Wako Pure Chemical Corporation) by dripping over 180 minutes. The temperature inside the reaction flask was 15° C. or lower. The resultant reaction liquid was extracted with ethyl acetate (900 mL) 3 times, and the extract was concentrated to thereby obtain a crude product of N-acryloyl sarcosine methyl ester.
Appearance: Pale yellow liquid
Yielded amount: 242.8 g
Yield: 68.8% by mass
GC-MS Analysis
Amount of N-acryloyl sarcosine methyl ester: 47.4 area %
Adduct ratio: 47.8 area %
Other components: 4.8 area %

Comparative Example 1-2

A crude product of N-acryloyl sarcosine methyl ester was obtained in the same manner as in Comparative Example 1-1, except that the cooling of the reaction system was replaced with cooling to about −5° C. using liquid nitrogen and ethanol, and the duration for dripping acrylic acid chloride was shortened to 15 minutes. The temperature inside the reaction flask was 15° C. or lower. The reaction progressed rapidly and foam was generated vigorously, probably because the acrylic acid chloride was dripped within the short period.
Appearance: Pale yellow liquid
Yielded amount: 307.3 g
Yield: 87.1% by mass
GC-MS Analysis
Amount of N-acryloyl sarcosine methyl ester: 79.7 area %
Adduct ratio: 14.1 area %
Other components: 6.2 area %

Comparative Example 1-3

A crude product of N-acryloyl sarcosine methyl ester was obtained in the same manner as in Comparative Example 1-1, except that the cooling of the reaction system was replaced with cooling to about −5° C. using liquid nitrogen and ethanol, and the duration for dripping acrylic acid chloride was shortened to 1 minute. The temperature inside the reaction flask was 15° C. or lower. The reaction progressed rapidly, and foam was generated vigorously to spout part of the foam generated out from the flask, probably because the acrylic acid chloride was dripped within the short period.
Appearance: Pale yellow liquid
Yielded amount: 322.2 g
Yield: 91.3% by mass
GC-MS Analysis
Amount of N-acryloyl sarcosine methyl ester: 99.4 area %
Adduct ratio: 0.4 area %
Other components: 0.2 area %

Comparative Example 1-41

A 1 L four-necked flask was charged with acrylic acid chloride (99.6 g, 1,100 mmol) and tetrahydrofuran (THF) (400 mL), and L-proline methyl ester-hydrochloride solids (165.6 g, 1,000 mmol, available from Combi-Brocks) were added to the resultant mixture with stirring, followed by cooling to a temperature ranging from −10° C. through −5° C. in an ice bath. Subsequently, a potassium carbonate aqueous solution [(207.3 g, 1.50 mol)+(water: 400 mL)] was added to the resultant by dripping over 10 minutes. The temperature inside the reaction flask was 15° C. or lower. The resultant reaction liquid was extracted with ethyl acetate (400 mL) 3 times, and the extract was concentrated to thereby obtain a crude product of N-acryloyl proline methyl ester.
Appearance: Pale yellow liquid
Yielded amount: 180.1 g
Yield: 68.9% by mass
GC-MS Analysis
Amount of N-acryloyl proline methyl ester: 96.4 area %
Adduct ratio: 3.4 area %
Other components: 0.2 area %

TABLE 1-1

| | Reaction scale Sar-Me/HCl*1 (moles) | Reaction scale L-Pro-Me/HCl*9 (moles) | Solvent | Water solubility of solvent to be mixed with water (g/100 mL) | Reagent dripping conditions (reagent: dripping duration) | Temperature inside flask (° C.) |
|---|---|---|---|---|---|---|
| Ex. 1-1 | 0.100 | — | Ethyl acetate + water | 8.00 | Sar-Me aq*5: 30 min | −3 or less |
| Ex. 1-2 | 2.245 | — | Ethyl acetate + water | 8.00 | Sar-Me aq*5: 30 min | 17 or less |
| Ex. 1-3 | 0.100 | — | Ethyl acetate + water | 8.00 | Sar-Me aq*6: 30 min | 13 or less |
| Ex. 1-4 | 0.100 | — | Ethyl acetate + water | 8.00 | Sar-Me aq*6: 10 min | 15 or less |
| Ex. 1-5 | 0.100 | — | Ethyl acetate + water | 8.00 | Sar-Me aq*7: 10 min | 20 or less |
| Ex. 1-6 | 0.500 | — | Ethyl acetate + water | 8.00 | Sar-Me aq*7: 10 min | 11 or less |
| Ex. 1-7 | 2.242 | — | Ethyl acetate + water | 8.00 | Sar-Me aq*7: 10 min | 12 or less |
| Ex. 1-8 | — | 2.245 | Ethyl acetate + water | 8.00 | Pro-Me aq*10: 15 min | 26 or less |
| Ex. 1-9 | 1.000 | — | Toluene + water | 0.07 | Sar-Me aq*7: 10 min | 15 or less |
| Ex. 1-10 | 1.100 | — | Cyclopentyl methyl ether + water | 1.10 | Sar-Me aq*7: 10 min | 15 or less |
| Ex. 1-11 | 1.100 | — | Butyl acetate + water | 0.70 | Sar-Me aq*7: 10 min | 15 or less |
| Ex. 1-12 | — | 1.000 | Methyl ethyl ketone + water | 29.00 | Pro-Me aq*10: 10 min | 15 or less |
| Comp. Ex. 1-1 | 2.235 | — | Water | — | AcCl*8: 180 min | 15 or less |
| Comp. Ex. 1-2 | 2.235 | — | Water | — | AcCl*8: 15 min | 15 or less |
| Comp. Ex. 1-3 | 2.235 | — | Water | — | AcCl*8: 1 min | 15 or less |
| Comp. Ex. 1-4 | — | 1.000 | THF + water | Miscible with water | Pro-Me aq*10: 10 min | 15 or less |

TABLE 1-2

| | Form of product (crude product) | Yield (% by mass) (crude product) | GC-MS results (area %) | | | Remarks (state of reaction etc.) |
|---|---|---|---|---|---|---|
| | | | Target*2 | Adduct*3 | Others*4 | |
| Ex. 1-1 | Colorless liq. | 91.5 | 97.1 | 0.2 | 2.7 | Foamed but not vigorously and reaction progressed mildly. |
| Ex. 1-2 | Pale yellow liq. | 72.4 | 86.5 | 9.5 | 4.0 | |
| Ex. 1-3 | Colorless liq. | 92.2 | 95.7 | 2.5 | 1.8 | |
| Ex. 1-4 | Colorless liq. | 93.8 | 96.7 | 1.4 | 1.9 | |
| Ex. 1-5 | Colorless liq. | 99.9 | 97.6 | 0.6 | 1.8 | |
| Ex. 1-6 | Pale yellow liq. | 98.9 | 99.8 | 0.0 | 0.2 | |
| Ex. 1-7 | Pale yellow liq. | 97.0 | 99.7 | 0.0 | 0.3 | |
| Ex. 1-8 | Pale yellow liq. | 94.7 | 99.5 | 0.0 | 0.5 | |

TABLE 1-2-continued

|  | Form of product (crude product) | Yield (% by mass) (crude product) | GC-MS results (area %) | | | Remarks (state of reaction etc.) |
|---|---|---|---|---|---|---|
|  |  |  | Target*2 | Adduct*3 | Others*4 |  |
| Ex. 1-9 | Pale yellow liq. | 92.7 | 98.1 | 1.9 | 0.0 | Hardly foamed and reaction progressed mildly. |
| Ex. 1-10 | Pale yellow liq. | 92.7 | 99.2 | 0.8 | 0.0 |  |
| Ex. 1-11 | Pale yellow liq. | 89.5 | 99.6 | 0.4 | 0.0 | Foamed but not vigorously and reaction progressed mildly. |
| Ex. 1-12 | Pale yellow liq. | 98.3 | 99.6 | 0.4 | 0.0 |  |
| Comp. Ex. 1-1 | Yellow liq. | 68.8 | 47.4 | 47.8 | 4.8 | Viscous product generated during extraction (poor separation) and strongly tinted. |
| Comp. Ex. 1-2 | Pale yellow liq. | 87.1 | 79.7 | 14.1 | 6.2 | Foamed very vigorously. |
| Comp. Ex. 1-3 | Pale yellow liq. | 91.3 | 99.4 | 0.4 | 0.2 | Foamed very vigorously (part of which was spouted) |
| Comp. Ex. 1-4 | Pale yellow liq. | 68.9 | 96.4 | 3.4 | 0.2 | Foamed but not vigorously and reaction progressed mildly. |

It was found from the results of Tables 1-1 and 1-2 that the synthesis method of the present disclosure, where the aqueous solution of at least one selected from the group consisting of the amino group-containing compound and the salt thereof was added to the mixture of the (meth)acrylic acid chloride and the solvent immiscible with water, could suppress generation of an adduct due to a side reaction, and could produce a (meth)acryl amide compound of high purity with high yield. In addition, it was found that the method of the present disclosure could control the progress of the reaction between (meth)acrylic acid chloride and the amino compound to be mild, although it was originally a very vigorous reaction. Moreover, it was found that the target (meth)acryl amide compound of high purity could be obtained with high yield by the method where the hydrochloride aqueous solution of the neutralization salt (hydrochloride) of the amino group-containing compound was added to the mixture including the (meth)acrylic acid chloride and the solvent immiscible with water, followed by adding the alkali aqueous solution, or the method where the solid neutralization salt (hydrochloride) of the amino group-containing compound was added, followed by dripping the alkali aqueous solution. Moreover, the yield and purity of the generated product could be improved by the solvent immiscible with water for use, and the excellent results could be obtained by using the solvent having solubility of 30 g/100 mL or less, and the generated product having the extremely high yield and purity could be obtained by using the solvent having the purity of from 2 g/100 mL through 30 g/100 mL. Meanwhile, it was confirmed that the reaction was progressed more mildly when the solvent having solubility of less than 2 g/100 mL in water.

*1: sarcosine methyl ester-hydrochloride (Sar-Me-HCl)
*2: N-acryloyl sarcosine methyl ester
*3: by-product formed of an adduct of N-acryloyl sarcosine methyl ester and sarcosine methyl ester
*4: total of other components detected by GC-MS
*5: The sarcosine methyl ester aqueous solution (aqueous solution of alkali neutralized product of sarcosine methyl ester-hydrochloride) was dripped for the predetermined period.
*6: After dripping the sarcosine methyl ester-hydrochloride aqueous solution, the potassium hydrocarbon aqueous solution was dripped for the predetermined period.
*7: After adding the sarcosine methyl ester-hydrochloride (solids), the potassium hydrocarbon aqueous solution was dripped for the predetermined period.
*8: Acrylic acid chloride (AcCl)
*9: L-proline methyl ester-hydrochloride (L-Pro-Me/HCl)
*10: After adding the L-proline methyl ester-hydrochloride (solids), the potassium hydrocarbon aqueous solution was dripped for the predetermined period.

It can be said that any of these method is a synthesis method has low hazard with a large scale and is suitable for industrialization, as the reaction is progressed relatively mildly.

Figure 1B:
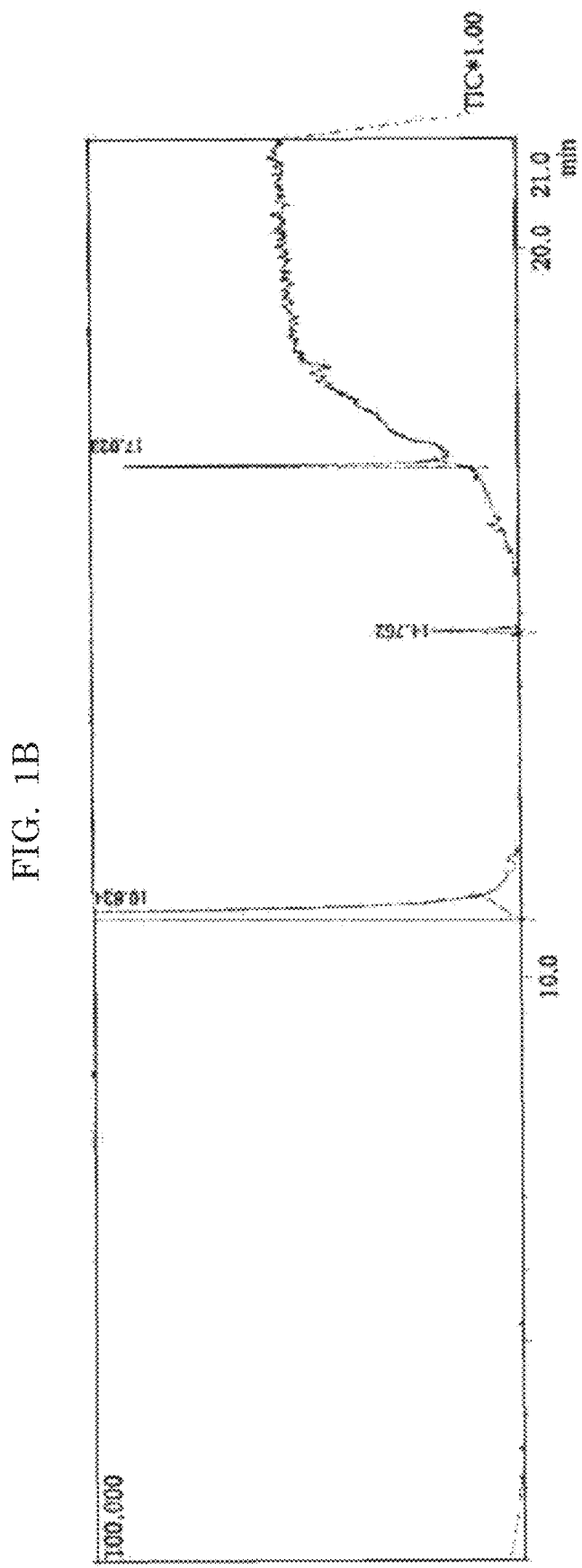
FIG. 1B is an enlarged view of FIG. 1A.
Figure 2B:
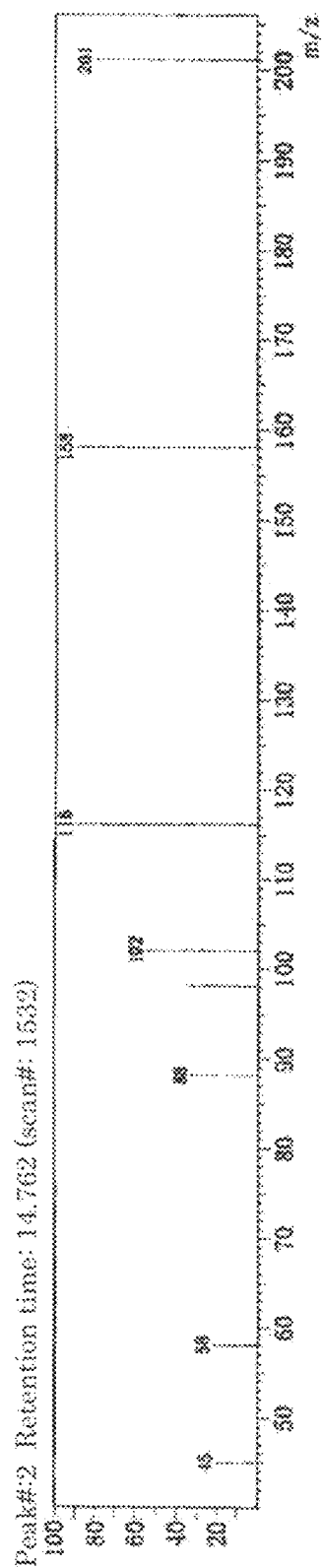
FIG. 2B is an MS chart for peaks with the retention time of 14.8 minutes detected in the GC-MS chromatograms of the compound obtained in Example 1-5.
Figure 2C:
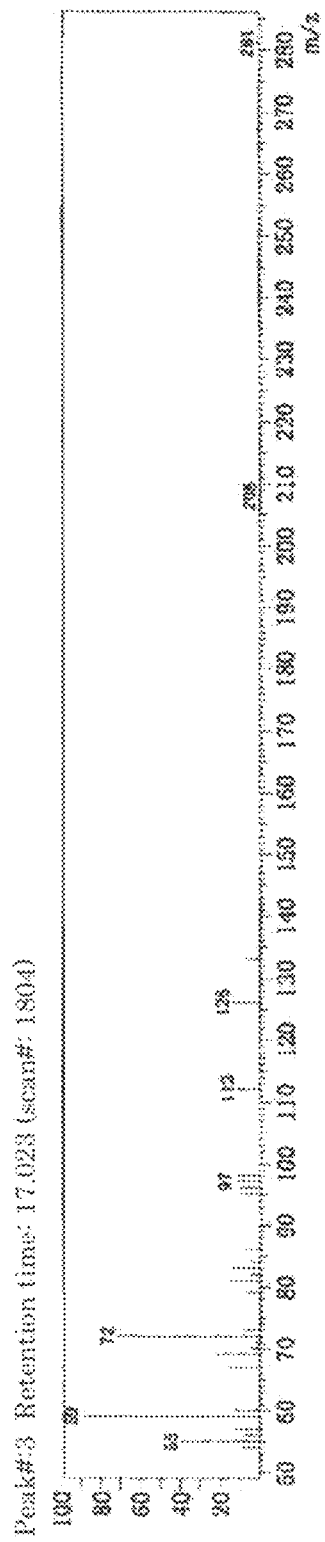
FIG. 2C is an MS chart for peaks with the retention time of 17.0 minutes detected in the GC-MS chromatograms of the compound obtained in Example 1-5.

The chromatogram exhibiting the result of CG-MS of the crude product of the N-acryloyl sarcosine methyl ester obtained in Example 1-5 is presented in FIG. 1A. Moreover, FIG. 1B depicts an enlarged view of FIG. 1A. Moreover, FIG. 2A is an MS chart of peaks with the retention time of 10.8 minutes detected in the chromatogram, FIG. 2B is an MS chart of peaks with the retention time of 14.8 minutes detected in the chromatogram, and FIG. 2C is an MS chart of peaks with the retention time of 17.0 minutes detected in the chromatogram.

Peaks with the retention time of 10.8 min.: N-acryloyl sarcosine methyl ester
Peaks with the retention time of 14.8 min.: by-product formed of an adduct of N-acryloyl sarcosine methyl ester and sarcosine methyl ester
Peaks with the retention time of 17.0 min.: other substances

[GC-MS Conditions]
Device: GCMS-QP2010 Plus (SHIMADZU)
Column: DB-5MS (Agilent J&W GC Columns) Length: 30 m/Diam.: 0.25 mm/Film: 0.25 μm
Heating program: Retaining at 50° C. for 0.5 min, then heating to 300° C. at 20° C./min, followed by retaining at 300° C. for 0.5 min.

The measurement was performed by means of the above-described device using the above-described columns with a scan mode.

Figure 3:
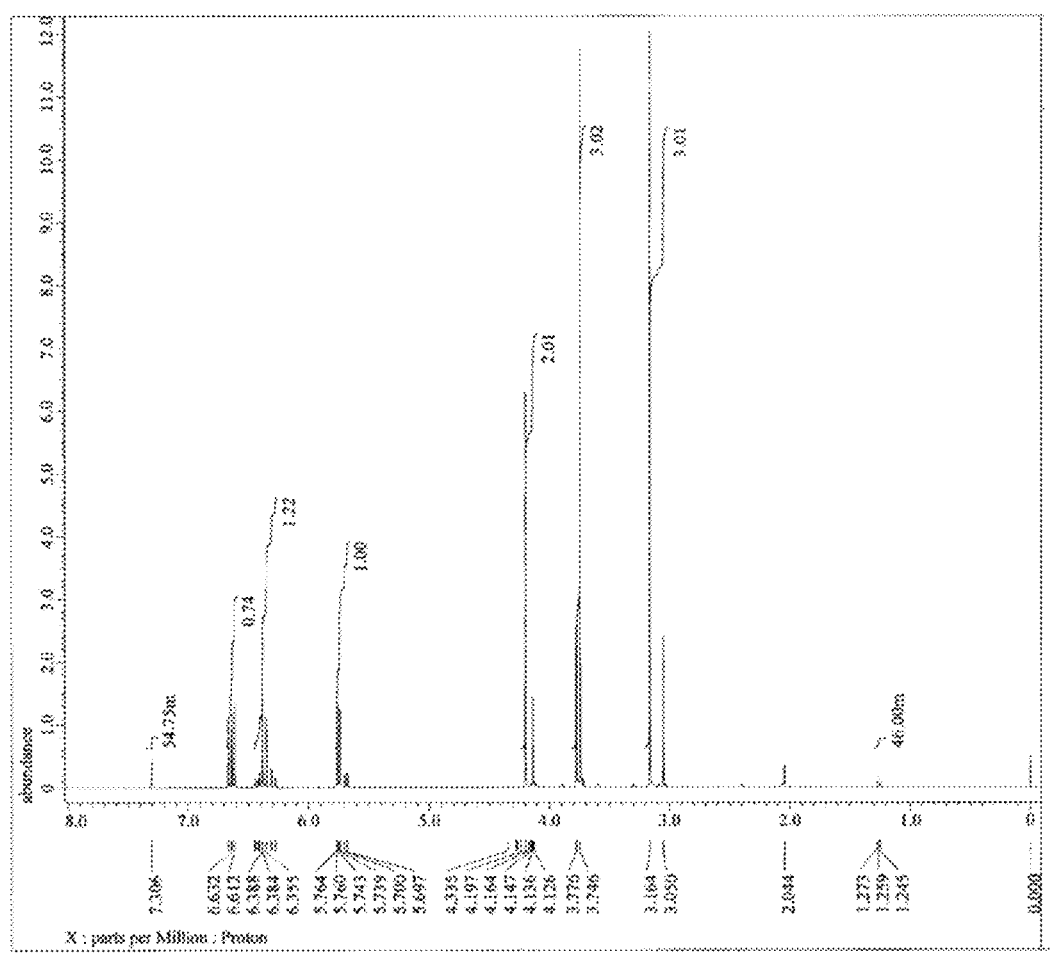
FIG. 3 is a $^1$H-NMR chart of the compound obtained in Example 1-7.

The ¹H-NMR chart of the crude product of N-acryloyl sarcosine methyl ester obtained in Example 1-7 is depicted in FIG. 3.

Device: ECX-500 (JEOL)
Frequency: 500 MHz

The sample was prepared using a solvent (chloroform-d), and an internal standard substance (0.03 vol % tetramethyl silane (TMS)-containing chloroform, D1, available from Merck). The measurement was performed on the sample by means of the above-mentioned device.

Figure 4A:
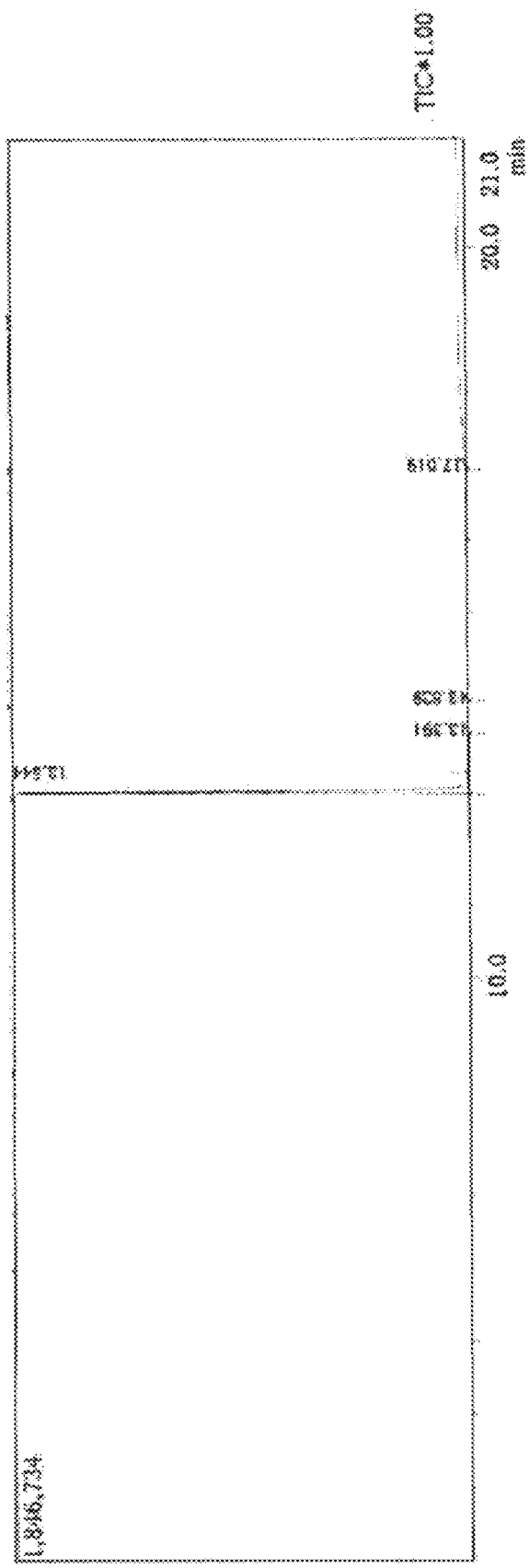
FIG. 4A is a GC-MS chromatogram of the compound obtained in Example 1-8.
Figure 4B:
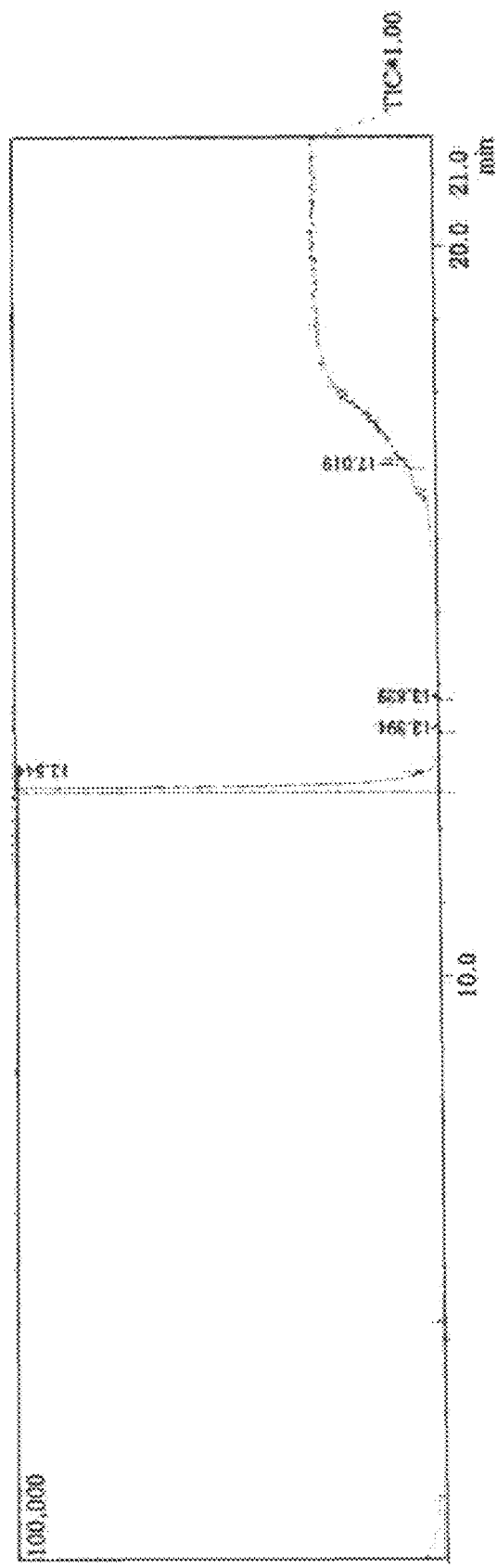
FIG. 4B is an enlarged view of FIG. 4A.
Figure 5B:
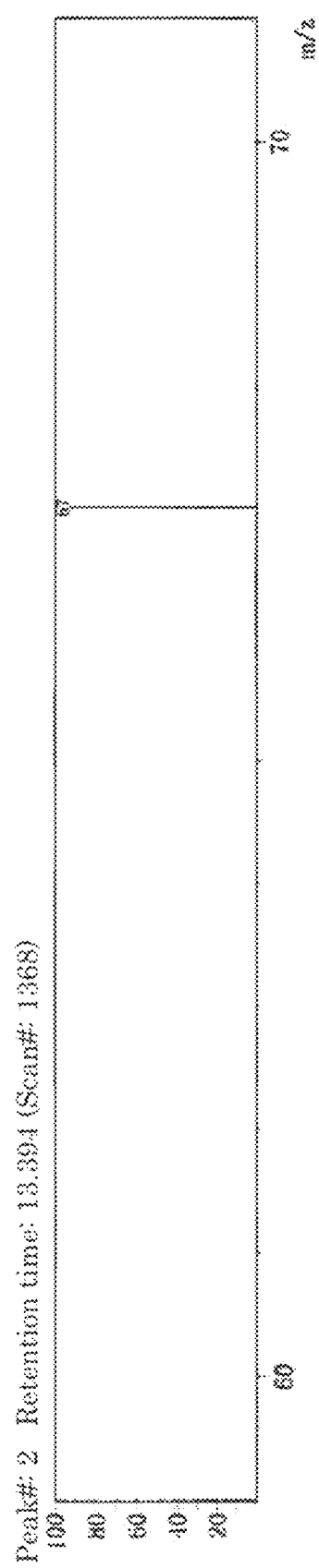
FIG. 5B is an MS chart for a peak with the retention time of 13.4 minutes detected in the GC-MS chromatogram of the compound obtained in Example 1-8.
Figure 5C:
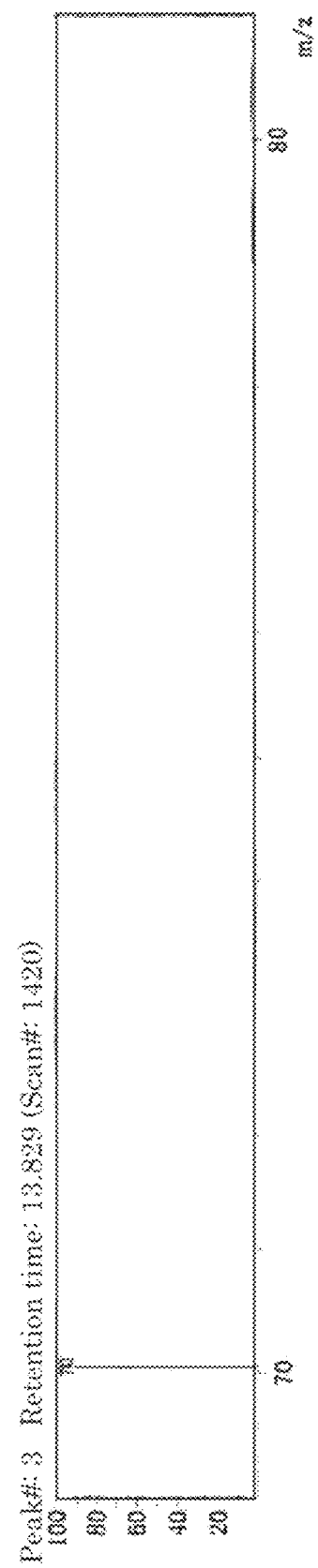
FIG. 5C is an MS chart for a peak with the retention time of 13.8 minutes detected in the GC-MS chromatogram of the compound obtained in Example 1-8.
Figure 5D:
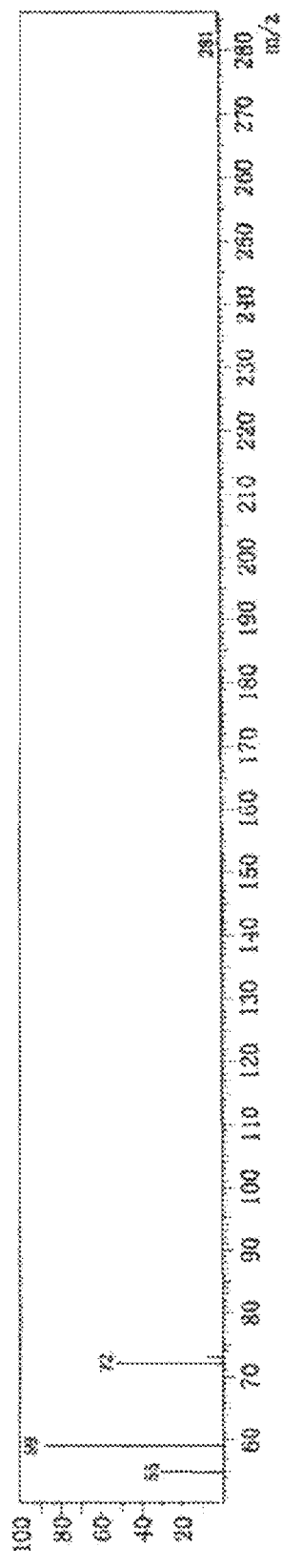
FIG. 5D is an MS chart for peaks with the retention time of 17.0 minutes detected in the GC-MS chromatogram of the compound obtained in Example 1-8.

In the same manner as with Example 1-5, the results of GC-MS of the crude product of N-acryloyl proline methyl ester obtained in Example 1-8 are depicted in FIGS. 4A and 4B and 5A to 5D. FIGS. 4A and 4B depict chromatograms, and FIGS. 5A to 5D depicts MS charts. Moreover, FIG. 6 depicts a ¹H-NMR chart of N-acryloyl proline methyl ester obtained in Example 1-8. Note that, 3 peaks appeared with the retention time of 13.4 min or later were peaks of components other than the Michael adduct, and therefore the determination of the structure for these 3 peaks was not carried out.

Peaks with the retention time of 12.5 min.: N-acryloyl proline methyl ester

Examples 2-1 to 2-8 and Comparative Examples 2-1 and 2-2

—Production of Active Energy Ray-Curable Composition—

Each (950 mg) of the active energy ray-curable compounds of Examples 1-1 to 1-8, and Comparative Examples 1-1 and 1-2, and 50 mg of a photopolymerization initiator (product name: IRGACURE907, component name: 2-methyl-1-[4-(methylthio)phenyl]-2-morpholinopropan-1-one, available from BASF Japan) were mixed using a magnetic stirrer to produce each pf active energy ray-curable compositions of Examples 2-1 to 2-8 and Comparative Examples 2-1 and 2-2.

Viscosity, photocurability, and adhesion of each of the active energy ray-curable compositions of Examples 2-1 to 2-8 and Comparative Examples 2-1 and 2-2 were evaluated in the following manner. The results are presented in Table 2.

<Measurement of Viscosity>

Viscosity of the obtained active energy ray-curable compound was measured by means of a cone and plate rotational viscometer (device name: VISCOMETER TVE-22L, available from Toki Sangyo Co., Ltd.) using a cone rotor (1° 34'×R24) at rotational speed of 50 rpm, with setting a temperature of constant-temperature circulating water to 25° C.

<Formation of Printed Image by Inkjet>

Each of the compositions was loaded in a composition storage container formed of a plastic, and the container was mounted in an image forming apparatus equipped with an inkjet head (MH5440, available from Ricoh Company Limited) serving as an ejection unit, UV-LED (LEDZERO available from Integration Technology Co., Ltd., wavelength: 395 nm, illuminance on the irradiation surface: 1.0 W/cm²) serving as an active energy ray irradiation unit, a controller configured to control ejection, and a supply path from the composition storage container to the inkjet head.

The temperature of the inkjet head was appropriately adjusted to control the viscosity of the composition to the range of from 10 mPa·s through 12 mPa·s. The composition was ejected onto a commercially available PET film (Cosmoshine A4100, available from TOYOBO CO. LTD., thickness: 188 μm), which was a generic film material, by inkjet printing to give a film thickness of 10 μm, followed by performing UV irradiation with the UV-LED, to thereby produce a print image.

<Evaluation of Curability>

A state where there was no tackiness upon touching the coated film with fingers was judged as being cured, and the integrated irradiation light dose required for curing was determined. The results are depicted in Table 2. A case where the integrated irradiation light dose required for curing was 1.0 J/cm² or less was determined as being practically usable.

<Evaluation of Adhesion>

Adhesion between the cured coated film and the base was evaluated in the following manner. A commercially available PET film (Ester Film E5100 available from TOYOBO CO., LTD., average thickness: 100 μm), which was a generic film material widely used as a wrapping material or an industrial material, was used. The active energy ray-curable composition was ejected onto a corona-treated surface of the PET film and onto a non-treated surface thereof by inkjet printing, followed by performing light irradiation with a UV irradiation device (LH6 (D bulb), available from Fusion Systems Japan Co., Ltd.) to cure and form a solid coated film. The resultant coated film was subjected to a measurement according to the cross-cut method specified in JIS-K-5600-5-6, and "adhesion" was evaluated based on the following evaluation criteria. The results are presented in Table 2.

[Evaluation Criteria]

A: There was no peeling observed.
B: Only small pealing in the range of 5% or greater but less than 20% relative to the entire area was observed.
C: Pealing in the range of 20% or greater but less than 50% relative to the entire area was observed.
D: Pealing in the range of 50% or greater relative to the entire area was observed.

TABLE 2

| Active energy ray-curable composition | (Meth)acrylamide composition | Viscosity (25° C., mPa•s) | Integrated irradiation light dose required for curing J/cm² | Adhesion |
| --- | --- | --- | --- | --- |
| Ex. 2-1 | Ex. 1-1 | 14.4 | 0.4 | A |
| Ex. 2-2 | Ex. 1-2 | 17.1 | 0.5 | B |
| Ex. 2-3 | Ex. 1-3 | 15.0 | 0.4 | A |
| Ex. 2-4 | Ex. 1-4 | 13.6 | 0.3 | A |
| Ex. 2-5 | Ex. 1-5 | 13.7 | 0.3 | A |
| Ex. 2-6 | Ex. 1-6 | 13.1 | 0.2 | A |
| Ex. 2-7 | Ex. 1-7 | 13.1 | 0.2 | A |
| Ex. 2-8 | Ex. 1-8 | 39.1 | 0.05 | A |
| Comp. Ex. 2-1 | Comp. Ex. 1-1 | 74.6 | 5.5 | B |
| Comp. Ex. 2-2 | Comp. Ex. 1-2 | 34.7 | 1.2 | C |

It was found from the results in Table 2 that the active energy ray-curable composition of the present disclosure had low viscosity, and excellent curability and adhesion to the base.

For example, the embodiments of the present disclosure are as follows.

<1> A method for producing a (meth)acrylic acid amide compound, the method including
adding at least one selected from the group consisting of an amino group-containing compound and a neutralization salt of the amino group-containing compound to a mixture comprising (meth)acrylic acid halide and an organic solvent immiscible with water to allow the (meth)acrylic acid halide and at least one selected from the group consisting of the amino group-containing compound and the neutralization salt of the amino group-containing compound to react with each other, to produce the (meth)acrylic acid amide compound.

<2> The method according to <1>, wherein at least one selected from the group consisting of the amino group-containing compound and the neutralization salt of the amino group-containing compound is an aqueous solution of at least one selected from the group consisting of the amino group-containing compound and the neutralization salt of the amino group-containing compound.

<3> The method according to <1> or <2>, further including adding an alkaline aqueous solution after adding at least one selected from the group consisting of the amino group-containing compound and the neutralization salt of the amino group-containing compound to the mixture.

<4> The method according to any one of <1> to <3>, wherein solubility of the organic solvent in water is 30 g/100 mL or less.

<5> The method according to any one of <1> to <4>, wherein the solubility of the organic solvent in water is 2 g/100 mL or greater but 30 g/100 mL or less.

<6> The method according to any one of <1> to <5>, wherein the organic solvent is at least one selected from the group consisting of ethyl acetate, toluene, cyclopentyl methyl ether, butyl acetate, and methyl ethyl ketone.

<7> The method according to any one of <1> to <6>, wherein the organic solvent is ethyl acetate.

<8> The method according to any one of <1> to <7>, wherein at least one selected from the group consisting of the amino group-containing compound and the neutralization salt of the amino group-containing compound is a compound comprising an amino group and a carboxylic acid ester structure.

<9> The method according to <8>, wherein the compound comprising an amino group and a carboxylic acid ester structure is an amino acid derivative having sarcosine as a mother nucleus.

<10> The method according to <8>, wherein the compound comprising an amino group and a carboxylic acid ester structure is an amino acid derivative having proline as a mother nucleus.

<11> A composition including:
a (meth)acrylic acid amide compound; and
an adduct of a (meth)acrylic acid amide compound and an amino group-containing compound,
wherein an amount of the (meth)acrylic acid amide compound is 95% by mass or greater, and an amount of the adduct of the (meth)acrylic acid amide compound and the amino group-containing compound is less than 5% by mass.

<12> An active energy ray-curable composition including the composition according to <11>.

The method for producing a (meth)acrylic acid amide compound according to any one of <1> to <10>, the composition according to <11>, and the active energy ray-curable composition according to <12> can solve the above-described various problems existing in the art and can achieve the object of the present disclosure.

What is claimed is:

1. A method for producing a (meth)acrylic acid amide compound, the method comprising:
   adding an aqueous solution of at least one compound selected from the group consisting of an amino group-containing compound and a neutralization salt of the amino group-containing compound,
   to a mixture including (meth)acrylic acid halide and an organic solvent immiscible with water,
   to allow the (meth)acrylic acid halide and at least one compound selected from the group consisting of the amino group-containing compound and the neutralization salt of the amino group-containing compound to react with each other,
   to produce the (meth)acrylic acid amide compound.

2. The method according to claim 1, further comprising adding an alkaline aqueous solution after adding the aqueous solution of the at least one compound selected from the group consisting of the amino group-containing compound and the neutralization salt of the amino group-containing compound to the mixture.

3. The method according to claim 1, wherein solubility of the organic solvent in water is 30 g/100 mL or less.

4. The method according to claim 1, wherein solubility of the organic solvent in water is 2 g/100 mL or greater but 30 g/100 mL or less.

5. The method according to claim 1, wherein the organic solvent is at least one selected from the group consisting of ethyl acetate, toluene, cyclopentyl methyl ether, butyl acetate, and methyl ethyl ketone.

6. The method according to claim 1, wherein the organic solvent is ethyl acetate.

7. The method according to claim 1, wherein at least one compound selected from the group consisting of the amino group-containing compound and the neutralization salt of the amino group-containing compound is a compound including an amino group and a carboxylic acid ester structure.

8. The method according to claim 7, wherein the compound comprising an amino group and a carboxylic acid ester structure is an amino acid derivative having sarcosine as a mother nucleus.

9. The method according to claim 7, wherein the compound comprising an amino group and a carboxylic acid ester structure is an amino acid derivative having proline as a mother nucleus.

10. The method according to claim 1, wherein the at least one compound selected from the group consisting of the amino group-containing compound and the neutralization salt of the amino group-containing compound is a compound including a carboxylic acid ester structure and an amino group which corresponds to an amino acid derivative having sarcosine or proline as a mother nucleus, and
    wherein solubility of the organic solvent in water is 30 g/100 mL or less.

11. The method according to claim 10, which includes the amino group which corresponding to a sarcosine mother-nucleus.

12. The method according to claim 10, which includes the amino group which corresponding to a proline mother-nucleus.

13. The method according to claim 10, wherein solubility of the organic solvent in water is 2 g/100 mL or greater but 30 g/100 mL or less.

14. The method according to claim 10, wherein the organic solvent is at least one selected from the group consisting of ethyl acetate, toluene, cyclopentyl methyl ether, butyl acetate, and methyl ethyl ketone.

15. The method according to claim 10, wherein the organic solvent is ethyl acetate.

16. The method according to claim 1, wherein the reaction takes place in a non-homogenous reaction system including the solvent immiscible with water and water.

17. The method according to claim 16, wherein an amidation reaction progresses at an interface between the organic solvent and water.

* * * * *